(12) United States Patent
Mou et al.

(10) Patent No.: US 12,042,758 B2
(45) Date of Patent: Jul. 23, 2024

(54) AIR PURIFICATION DEVICE

(71) Applicant: Microjet Technology Co., Ltd., Hsinchu (TW)

(72) Inventors: Hao-Jan Mou, Hsinchu (TW); Chin-Chuan Wu, Hsinchu (TW); Ching-Sung Lin, Hsinchu (TW); Yung-Lung Han, Hsinchu (TW); Chi-Feng Huang, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 97 days.

(21) Appl. No.: 17/671,759

(22) Filed: Feb. 15, 2022

(65) Prior Publication Data

US 2022/0305423 A1   Sep. 29, 2022

(30) Foreign Application Priority Data

Mar. 29, 2021 (TW) .................................. 110111419

(51) Int. Cl.
*B01D 53/04* (2006.01)
*B01D 46/00* (2022.01)
*B01D 46/44* (2006.01)
*B01D 46/46* (2006.01)
(Continued)

(52) U.S. Cl.
CPC ....... *B01D 46/442* (2013.01); *B01D 46/0036* (2013.01); *B01D 46/0047* (2013.01);
(Continued)

(58) Field of Classification Search
CPC .............. B01D 46/442; B01D 46/0036; B01D 46/0047; B01D 46/46; B01D 53/0446;
(Continued)

(56) References Cited

U.S. PATENT DOCUMENTS 4,604,110 A * 8/1986 Frazier ................. F24F 1/0071
  55/471
2004/0146436 A1* 7/2004 Ham ................... B01D 53/0407
  422/177
(Continued)

FOREIGN PATENT DOCUMENTS

CN   101296711 A   10/2008
CN   102886183 A   1/2013
(Continued)

OTHER PUBLICATIONS

Machine-generated English translation of CN 207849603 U, published Sep. 2018 (Year: 2018).*

(Continued)

*Primary Examiner* — Frank M Lawrence, Jr.
(74) *Attorney, Agent, or Firm* — Birch, Stewart, Kolasch & Birch, LLP

(57) ABSTRACT

An air purification device includes a device main body, a purification filter and a gas detection module. The device main body includes a gas-inlet opening and a gas-outlet opening. The purification filter is disposed in the device main body and includes at least one activated carbon layer and at least one zeolite layer stacked on each other, wherein the activated carbon layer filters and absorbs suspended particles contained in an air introduced through the gas-inlet opening, and the zeolite layer includes porous structures with hydrophobic property for controlling and absorbing volatile organic compounds contained in the air introduced through the gas-inlet opening, thereby a purified gas is generated from the air and is discharged through the gas-outlet opening. The gas detection module is disposed in the device main body for detecting and obtaining a gas quality data of the air passing through the gas-inlet opening and outputting the gas quality data.

8 Claims, 20 Drawing Sheets

(51) Int. Cl.
*G01N 15/00* (2006.01)
*G01N 15/075* (2024.01)

(52) U.S. Cl.
CPC ......... *B01D 46/46* (2013.01); *B01D 53/0446* (2013.01); *B01D 53/0454* (2013.01); *B01D 2253/102* (2013.01); *B01D 2253/108* (2013.01); *B01D 2257/708* (2013.01); *G01N 2015/0046* (2013.01); *G01N 15/075* (2024.01)

(58) Field of Classification Search
CPC ................ B01D 53/0454; B01D 53/04; B01D 2253/102; B01D 2253/108; B01D 2257/708; B01D 53/30; B01D 2253/34; B01D 2258/06; B01D 53/0415; G01N 2015/0046; G01N 2015/0693; G01N 1/22; G01N 15/0205; G01N 15/06; G01N 33/0004; G01N 33/0009; G01N 33/0047; G01N 2015/0065; F24F 8/108
USPC ............................................ 96/111, 132, 134
See application file for complete search history.

(56) References Cited

U.S. PATENT DOCUMENTS

| | | | | |
|---|---|---|---|---|
| 2005/0011361 A1* | 1/2005 | Jung | .................. | B01D 53/0446 96/135 |
| 2010/0005965 A1* | 1/2010 | Kodde | .................. | B01D 53/04 95/148 |
| 2013/0092029 A1* | 4/2013 | Morgan | .................... | E03F 5/08 96/111 |
| 2021/0096052 A1* | 4/2021 | Mou | .................. | G01N 15/1459 |
| 2021/0254845 A1 | 8/2021 | Mou et al. | | |

FOREIGN PATENT DOCUMENTS

| | | |
|---|---|---|
| CN | 103776103 A | 5/2014 |
| CN | 203928175 U | 11/2014 |
| CN | 104315596 A | 1/2015 |
| CN | 107202375 A | 9/2017 |
| CN | 108167958 A | 6/2018 |
| CN | 211576880 U | 9/2020 |
| JP | 11-207130 A | 8/1999 |
| TW | I708934 B | 11/2020 |
| TW | I720820 B | 3/2021 |

OTHER PUBLICATIONS

Machine-generated English translation of CN 108167958 A, published Jun. 2018.*
Extended European Search Report for European Application No. 22162469.5, dated Sep. 13, 2022.

* cited by examiner

AIR PURIFICATION DEVICE

FIELD OF THE INVENTION

The present disclosure relates to an air purification device, and more particularly to a device adapted to filter an air for performing the functions of gas detection and purifying harmful gases in an activity space.

BACKGROUND OF THE INVENTION

In recent years, people pay more and more attention to the air quality around our daily lives. Particulate matter (PM), such as $PM_1$, $PM_{2.5}$, $PM_{10}$, and gases, such as carbon dioxide, total volatile organic compounds (TVOC), formaldehyde etc., are all exposed in the environment and might affect the human health, and even endanger people's lives seriously. It is worth noting that the air quality in the activity space has gradually attracted people's attention. Therefore, providing an air purification device capable of purifying and improving the air quality to prevent from breathing harmful gases in the activity space through filtering the air in the activity space in real time and purifying the air in the activity space quickly when the air quality is poor, so as to improve the efficiency for purifying the air is an issue of concern developed in the present disclosure.

SUMMARY OF THE INVENTION

The present disclosure provides an air purification device for filtering and purifying suspended particles (such as particulate matter, $PM_{2.5}$) and volatile organic compounds (such as VOCs) contained in the air through a purification filter disposed therein, so as to generate a purified gas after the filtration and purification of the air.

The major object of the present disclosure is to provide an air purification device including a device main body, a purification filter and a gas detection module. The device main body includes at least one gas-inlet opening and at least one gas-outlet opening. The purification filter is disposed in the device main body and includes at least one activated carbon layer and at least one zeolite layer stacked on each other. The activated carbon layer filters and absorbs suspended particles contained in an air introduced into the device main body through the gas-inlet opening, and the zeolite layer includes porous structures with hydrophobic property for controlling and absorbing volatile organic compounds contained in the air introduced into the device main body through the gas-inlet opening, thereby a purified gas is generated from the introduced air and is discharged through the gas-outlet opening. The gas detection module is disposed in the device main body for detecting and obtaining a gas quality data of the air passing through the gas-inlet opening and outputting the gas quality data.

BRIEF DESCRIPTION OF THE DRAWINGS

The above contents of the present disclosure will become more readily apparent to those ordinarily skilled in the art after reviewing the following detailed description and accompanying drawings, in which.

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
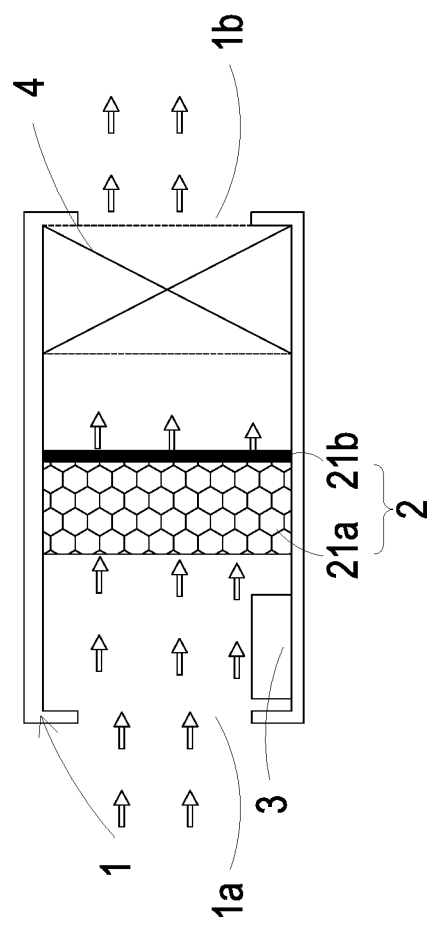
FIG. 1 is a schematic cross-sectional view illustrating an air purification device according to an embodiment of the present disclosure.
Figure 2:
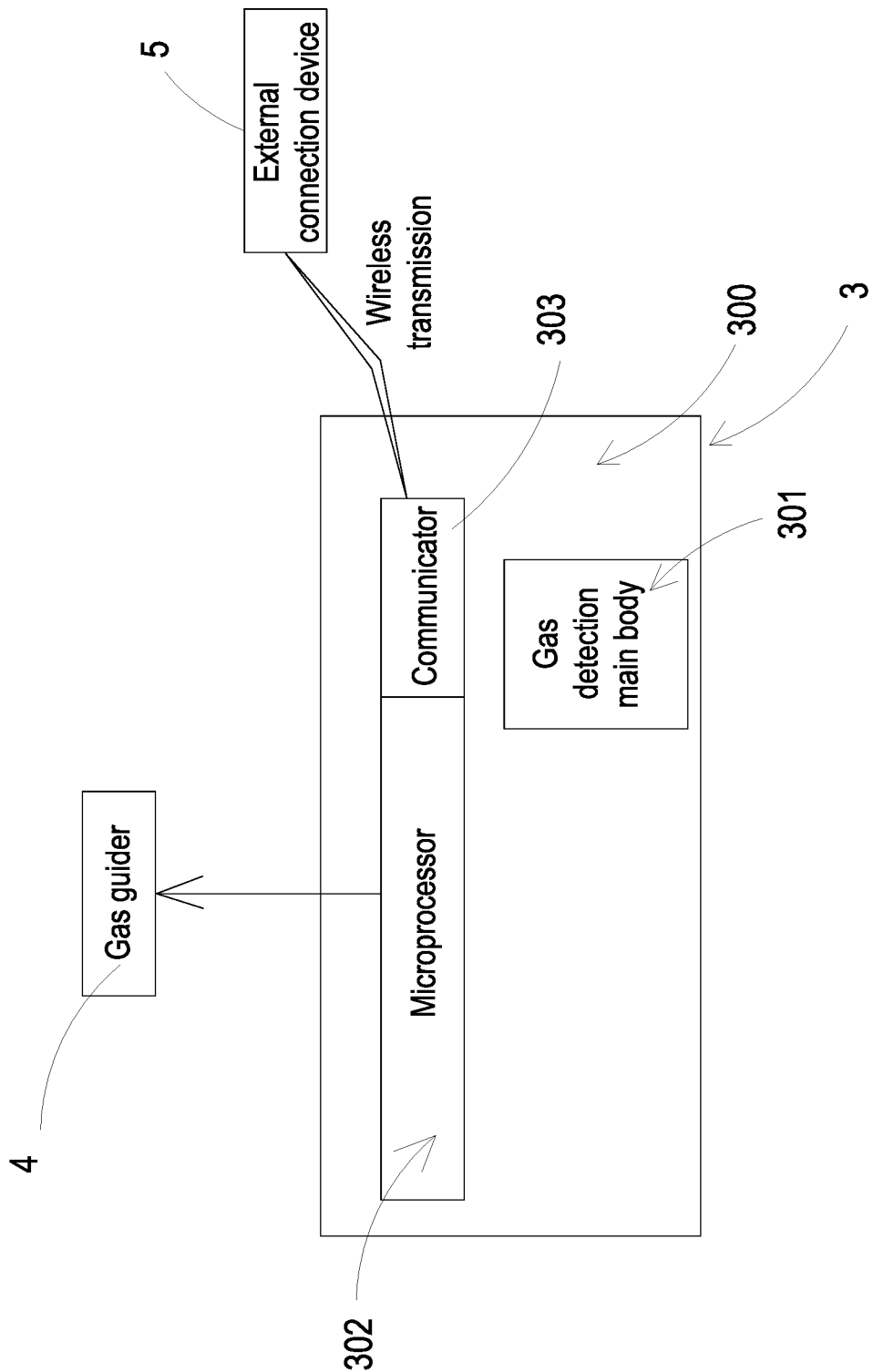
FIG. 2 is block diagram illustrating an electrical connection of a gas detection module according to an embodiment of the present disclosure.

Please refer to FIG. 1 and FIG. 2. The present disclosure provides an air purification device for filtering an air. The air purification device includes a device main body 1, a purification filter 2, a gas detection module 3 and a gas guider 4.

The device main body 1 mentioned above includes at least one gas-inlet opening 1a and at least one gas-outlet opening 1b.

The purification filter 2 mentioned above is disposed in the device main body 1 and includes at least one activated carbon layer 21a and at least one zeolite layer 21b. The activated carbon layer 21a filters and absorbs suspended particles (such as particulate matter, $PM_{2.5}$) contained in the air introduced into the device main body 1 through the gas-inlet opening 1a. The zeolite layer 21b includes porous structures with hydrophobic property for controlling and absorbing volatile organic compounds (such as VOCs) contained in the air introduced into the device main body 1 through the gas-inlet opening 1a. Consequently, a purified gas is generated from the introduced-in air.

In some embodiments, the purification filter 2 includes one single activated carbon layer 21a and a plurality of zeolite layers 21b stacked on each other for improving the efficiency of absorption and purification of the suspended particles (particulate matter, $PM_{2.5}$) and the volatile organic compounds (VOCs) contained in the air. In some other embodiments, the purification filter 2 includes a plurality of activated carbon layers 21a and one single zeolite layer 21b stacked on each other for improving the efficiency of absorption and purification of the suspended particles (particulate matter, $PM_{2.5}$) and the volatile organic compounds (VOCs) contained in the air. In some other embodiments, the purification filter 2 includes a plurality of activated carbon layers 21a and a plurality of plurality of zeolite layers 21b stacked on each other for improving the efficiency of absorption and purification of the suspended particles (particulate matter, $PM_{2.5}$) and the volatile organic compounds (VOCs) contained in the air.

The gas guider 4 mentioned above is disposed in the device main body 1 adjacent to the gas-outlet opening 1b. The gas guider 4 introduces the air to enter the device main body 1 and pass through the purification filter 2, so as to filter and purify the air and generate the purified gas. Furthermore, the purified gas introduced by the gas guider 4 is discharged through the gas-outlet opening 1b.

The gas detection module 3 mentioned above is disposed in the device main body 1 adjacent to the gas-inlet opening 1a. The gas detection module 3 detects and obtains gas quality data and outputs the gas quality data to the gas guider 4. Based on the gas quality data, the gas guider 4 intelligently determines whether it is to be enabled or disabled to guide the air for filtration and purification.

Figure 3:
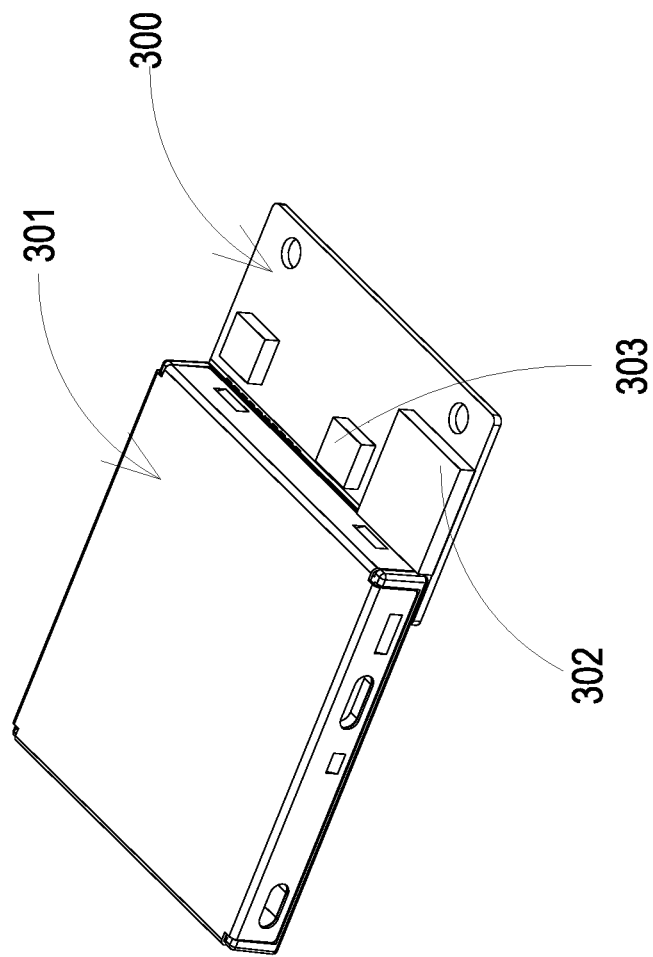
FIG. 3 is a schematic view illustrating an assembled gas detection module according to an embodiment of the present disclosure.
Figure 4A:
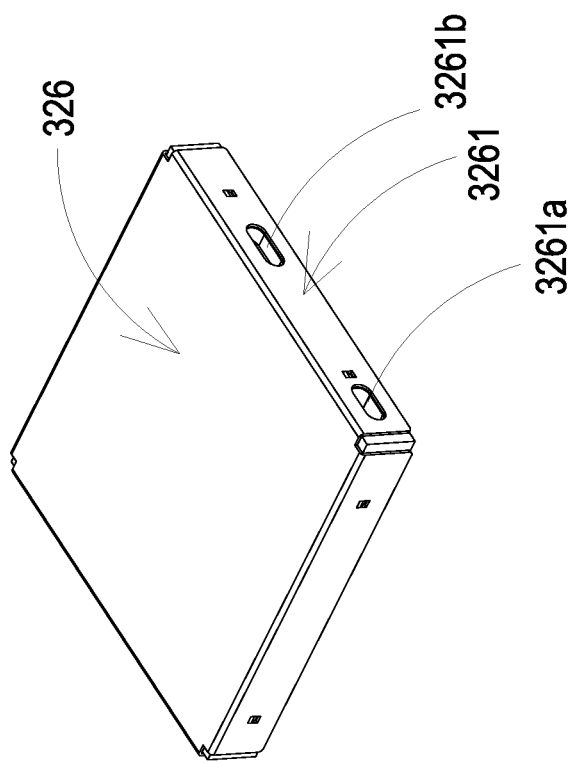
FIG. 4A is a schematic view illustrating an assembled gas detection main body according to an embodiment of the present disclosure.
Figure 4B:
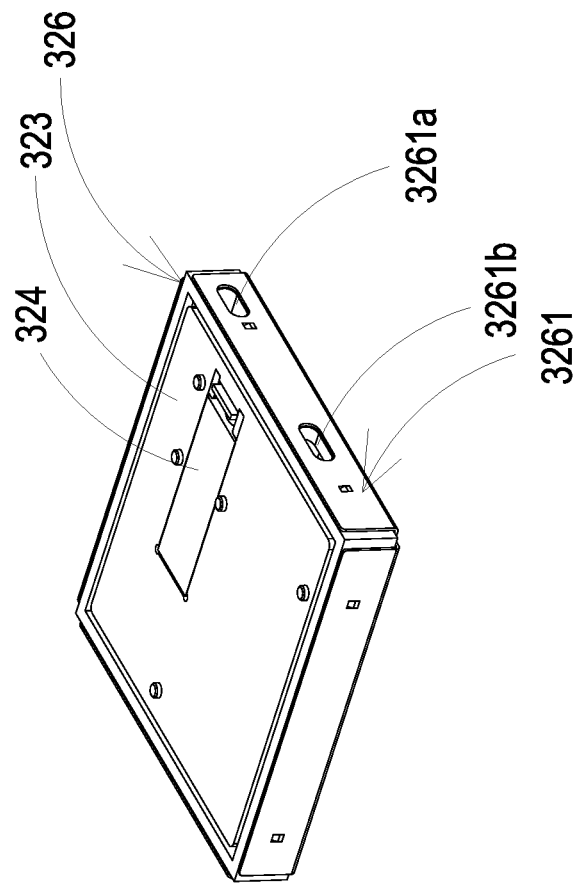
FIG. 4B is a schematic view illustrating the assembled gas detection main body according to the embodiment of the present disclosure from another view angle.
Figure 4C:
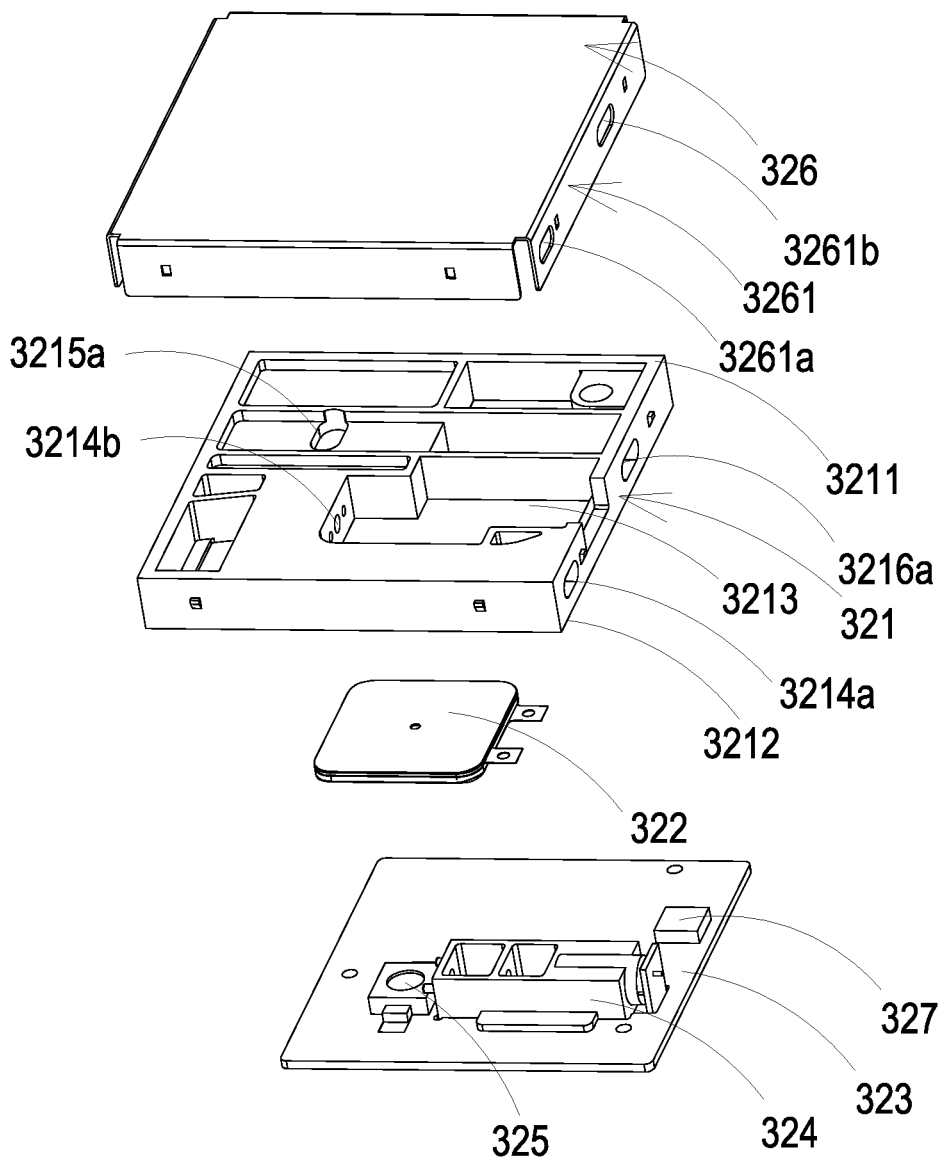
FIG. 4C is a schematic exploded view illustrating the gas detection main body according to the embodiment of the present disclosure.
Figure 5A:
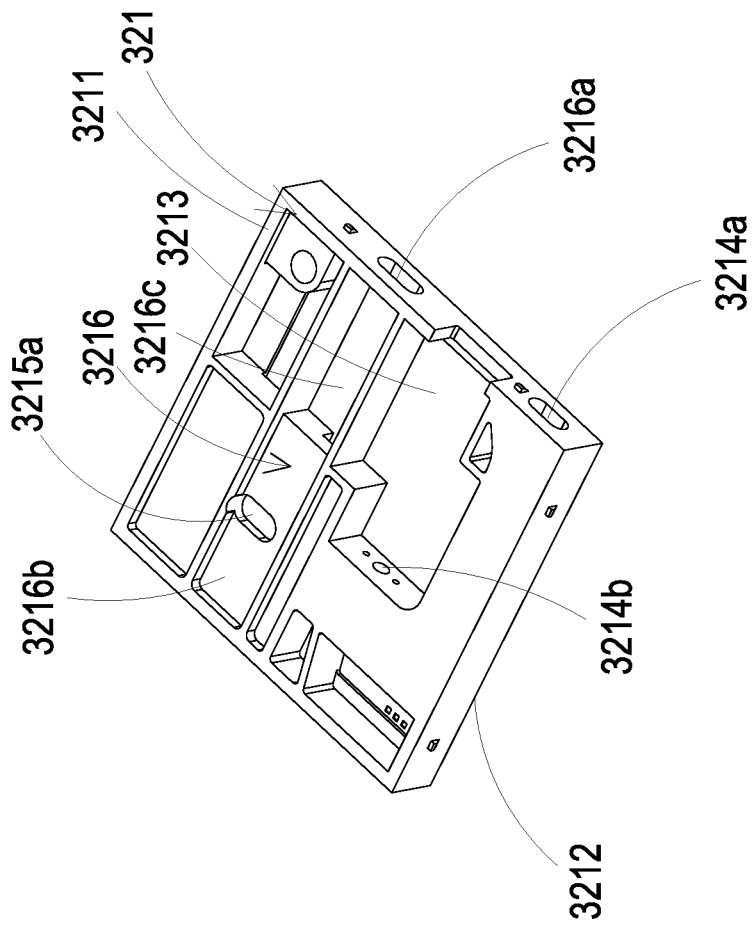
FIG. 5A is a schematic view illustrating a base according to an embodiment of the present disclosure.
Figure 5B:
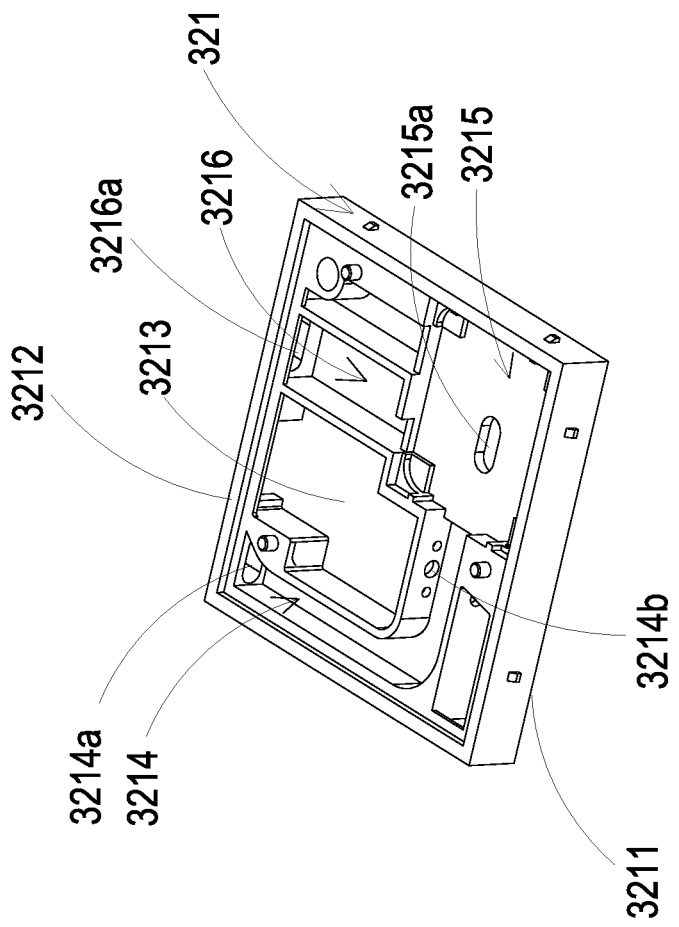
FIG. 5B is a schematic view illustrating the base according to the embodiment of the present disclosure from another view angle.
Figure 6:
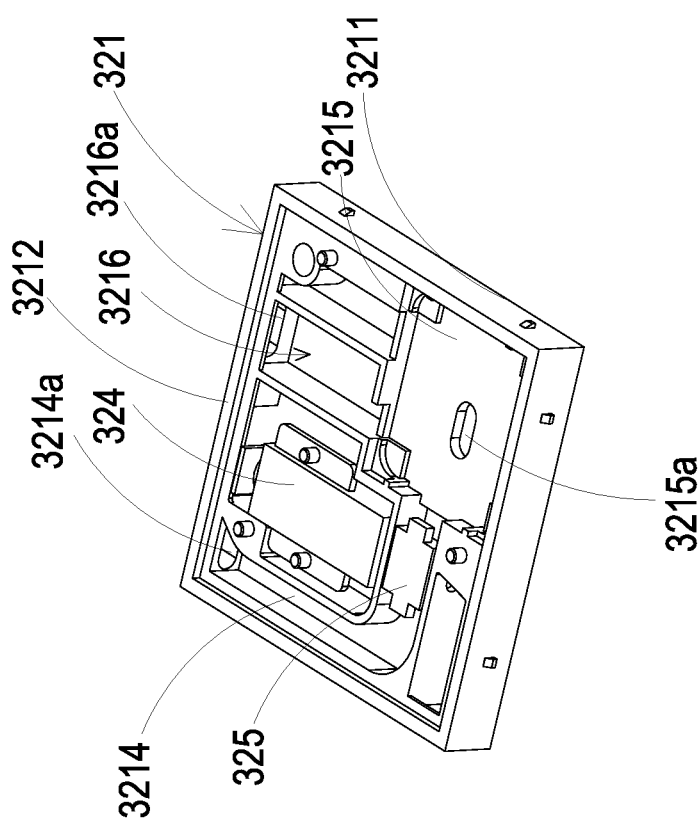
FIG. 6 is a schematic view illustrating the base with a laser component installed therein according to the embodiment of the present disclosure.
Figure 7A:
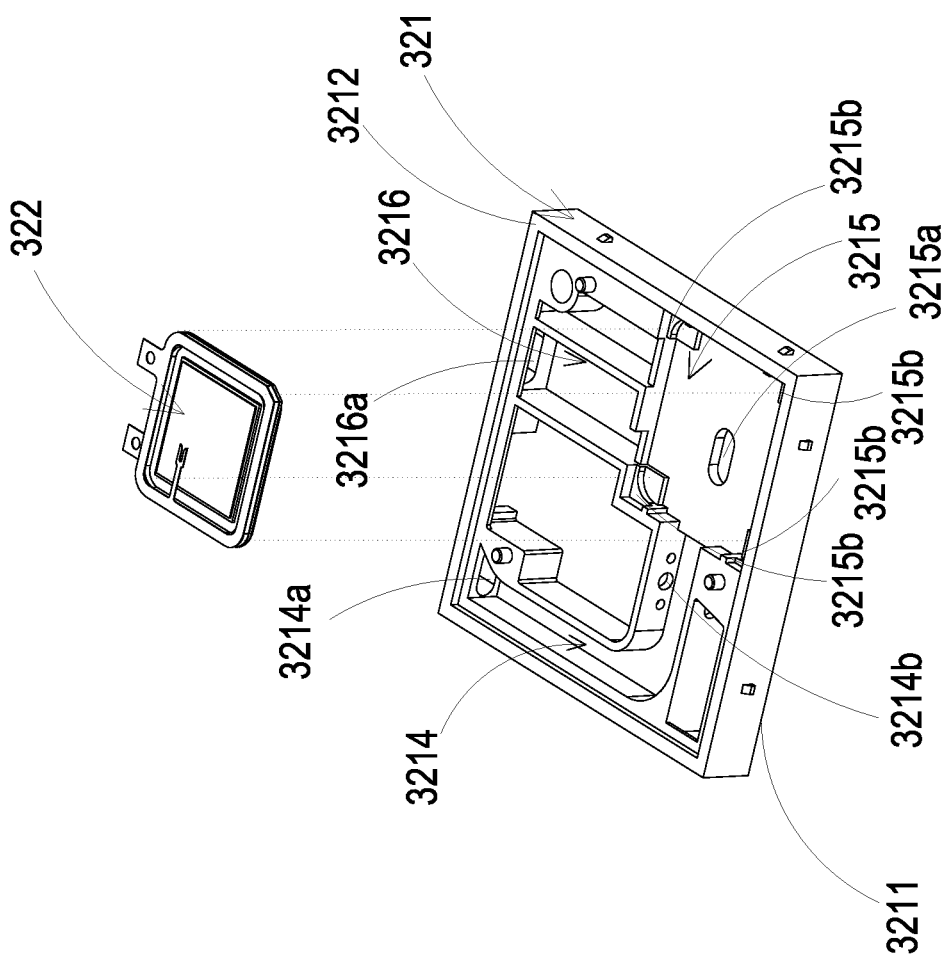
FIG. 7A is a schematic exploded view illustrating a piezoelectric actuator and the base according to an embodiment of the present disclosure.
Figure 7B:
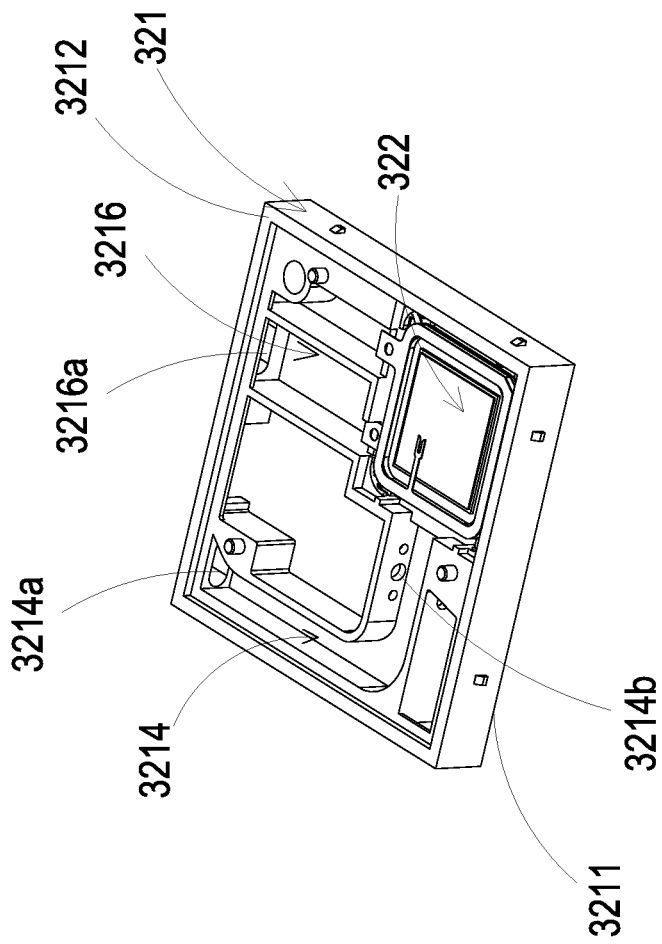
FIG. 7B is a schematic view illustrating the combination of the piezoelectric actuator and the base according to the embodiment of the present disclosure.
Figure 8A:
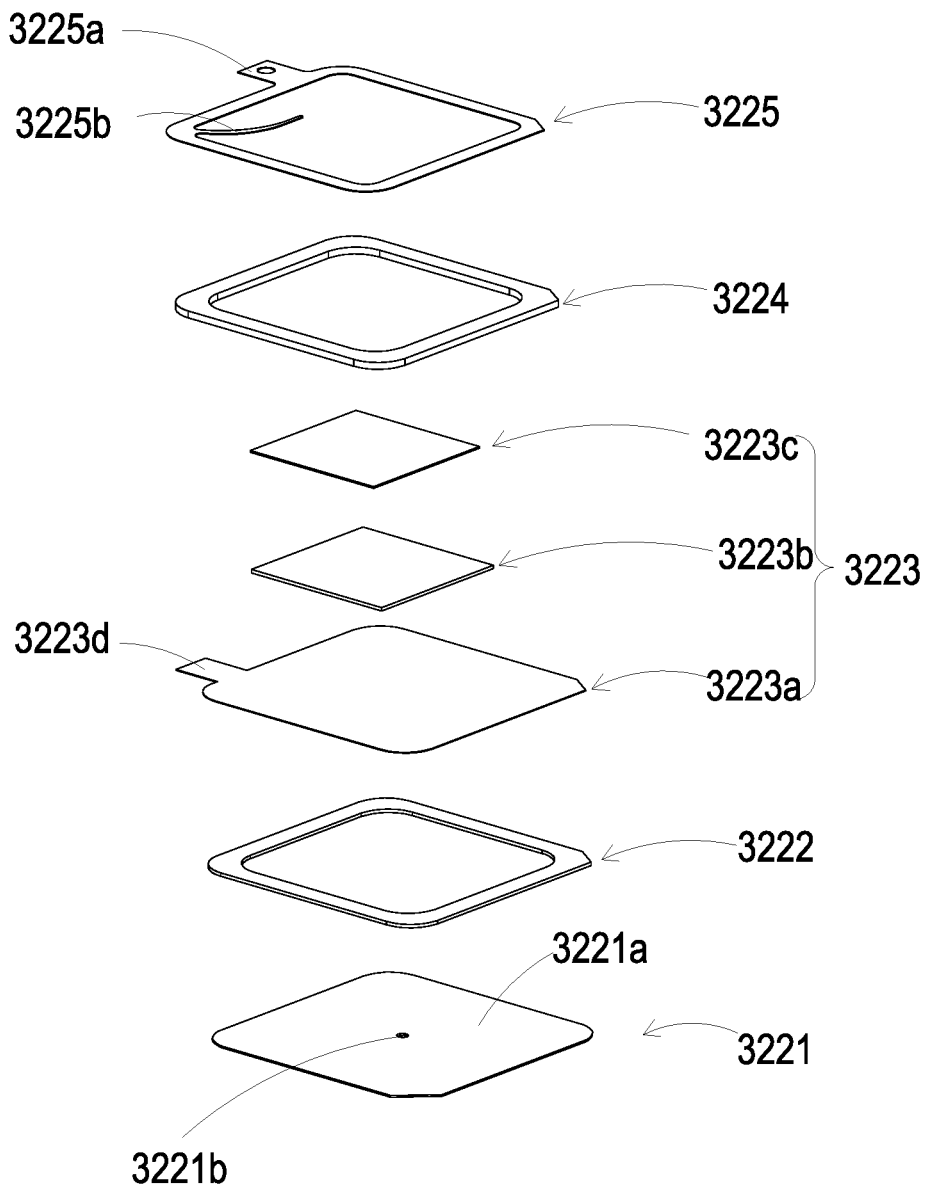
FIG. 8A is a schematic exploded view illustrating the piezoelectric actuator according to an embodiment of the present disclosure.
Figure 8B:
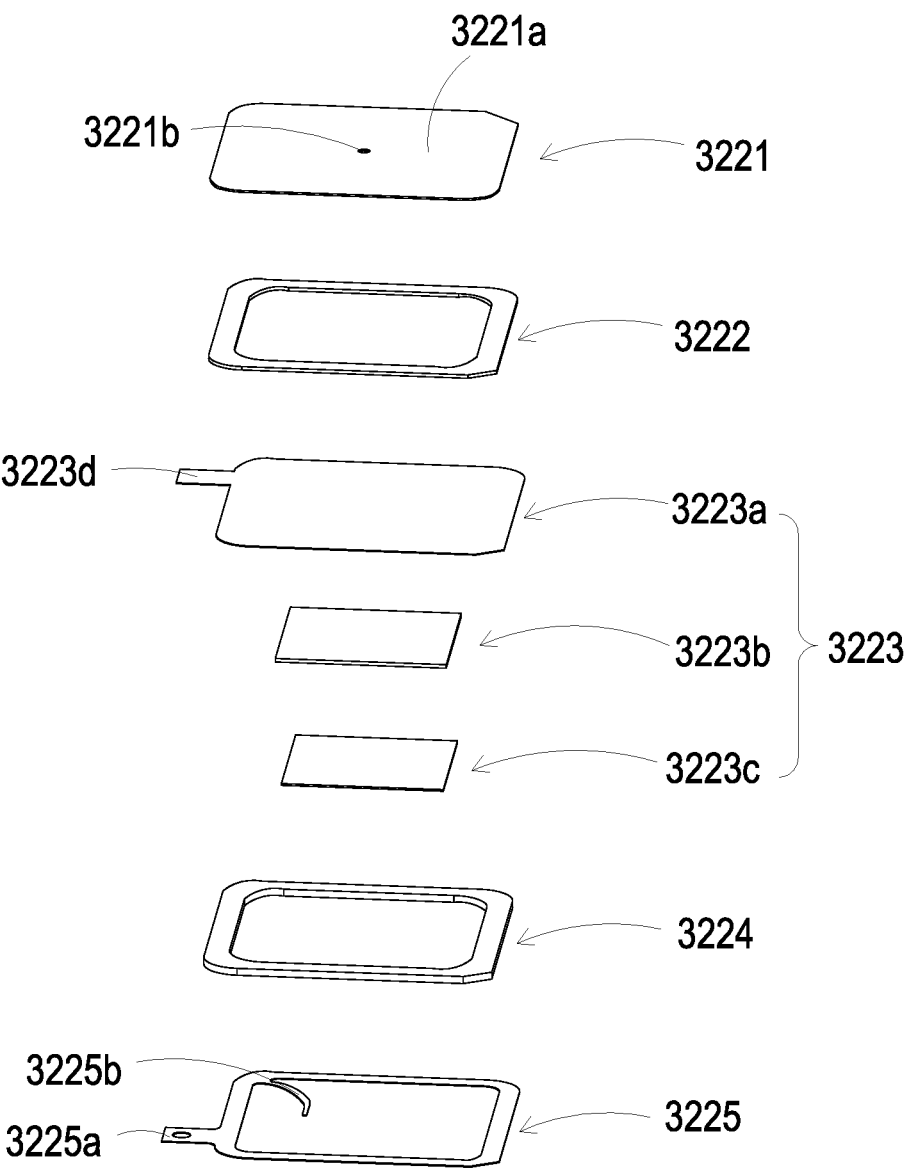
FIG. 8B is a schematic exploded view illustrating the piezoelectric actuator according to the embodiment of the present disclosure from another view angle.

Please refer to FIG. 2 to FIG. 3. The gas detection module 3 includes a control circuit board 300, a gas detection main body 301, a microprocessor 302 and a communicator 303. The gas detection main body 301, the microprocessor 302 and the communicator 303 are integrally packaged on the control circuit board 300 and electrically connected with each other. The microprocessor 302 and the communicator 303 are disposed on the control circuit board 300. The microprocessor 23 controls a detection operation of the gas detection main body 301, the gas detection main body 301 detects a polluted gas and outputs the gas quality data, and the microprocessor 302 receives, computes and processes the gas quality data and provides to the communicator 303, so as to further transmit to an external connection device 5. The external connection device 5 displays and records the gas quality data, and provides an alert notification based on the gas quality data.

Furthermore, please refer to FIG. 4A to FIG. 9A. The gas detection main body 301 includes a base 321, a piezoelectric actuator 322, a driving circuit board 323, a laser component 324, a particulate sensor 325, an outer cover 326 and a gas sensor 327. The base 321 includes a first surface 3211, a second surface 3212, a laser loading region 3213, a gas-inlet groove 3214, a gas-guiding-component loading region 3215 and a gas-outlet groove 3216. In the embodiment, the first surface 3211 and the second surface 3212 are two surfaces opposite to each other. In the embodiment, the laser loading region 3213 is hollowed out from the first surface 3211 to the second surface 3212. The outer cover 326 covers the base 321 and includes a lateral plate 3261. The lateral plate 3261 includes an inlet opening 3261a and an outlet opening 3261b. The gas-inlet groove 3214 is concavely formed from the second surface 3212 and disposed adjacent to the laser loading region 3213. The gas-inlet groove 3214 includes a gas-inlet 3214a in communication with an environment outside the base 321, and is spatially corresponding in position to the inlet opening 3261a of the outer cover 326. Two transparent windows 3214b are respectively opened on two lateral walls of the gas-inlet groove 3214 and are in communication with the laser loading region 3213. Therefore, as the first surface 3211 of the base 321 is covered and attached by the outer cover 326 and the second surface 3212 of the base 321 is covered and attached by the driving circuit board 323, an inlet path is collaboratively defined by the gas-inlet groove 3214, the outer cover 326, and the driving circuit board 323.

In the embodiment, the gas-guiding-component loading region 3215 is concavely formed from the second surface 3212 and in communication with the gas-inlet groove 3214. A ventilation hole 3215a penetrates a bottom surface of the gas-guiding-component loading region 3215, and four positioning protrusions 3215b are disposed at four corners of the gas-guiding-component loading region 3215, respectively. In the embodiment, the gas-outlet groove 3216 includes a gas-outlet 3216a, and the gas-outlet 3216a is spatially corresponding to the outlet opening 3261b of the outer cover 326. The gas-outlet groove 3216 includes a first section 3216b and a second section 3216c. The first section 3216b is concavely formed from a region of the first surface 3211 spatially corresponding to a vertical projection area of the gas-guiding-component loading region 3215. The second section 3216c is hollowed out from the first surface 3211 to the second surface 3212 in a region where the first surface 3211 is misaligned with the vertical projection area of the gas-guiding-component loading region 3215 and extended therefrom. The first section 3216b and the second section 3216c are connected to form a stepped structure. Moreover, the first section 3216b of the gas-outlet groove 3216 is in communication with the ventilation hole 3215a of the gas-guiding-component loading region 3215, and the second section 3216c of the gas-outlet groove 3216 is in communication with the gas-outlet 3216a. In that, when the first surface 3211 of the base 321 is attached and covered by the outer cover 326 and the second surface 3212 of the base 321 is attached and covered by the driving circuit board 323, the gas-outlet groove 3216, the outer cover 326 and the driving circuit board 323 collaboratively define an outlet path.

Furthermore, the laser component 324 and the particulate sensor 325 mentioned above are disposed on the driving circuit board 323 and located within the base 321. In order to clearly describe and illustrate the positions of the laser component 324 and the particulate sensor 325 in the base 321, the driving circuit board 323 is specifically omitted. The laser component 324 is accommodated in the laser loading region 3213 of the base 321, and the particulate sensor 325 is accommodated in the gas-inlet groove 3214 of the base 321 and is aligned to the laser component 324. In addition, the laser component 324 is spatially corresponding to the transparent window 3214b, thereby a light beam emitted by the laser component 324 passes through the transparent window 3214b and irradiates into the gas-inlet groove 3214. Furthermore, the light beam path extends from the laser component 324 and passes through the transparent window 3214b in an orthogonal direction perpendicular to the gas-inlet groove 3214. In the embodiment, a projecting light beam emitted from the laser component 324 passes through the transparent window 3214b and enters the gas-inlet groove 3214 to irradiate the gas in the gas-inlet groove 3214. When the suspended particles contained in the gas are irradiated and generate scattered light spots, the scattered light spots are detected and calculated by the particulate sensor 325 for obtaining the detection data of the gas. Moreover, the gas sensor 327 is positioned and disposed on the driving circuit board 323 and electrically connected to the driving circuit board 323, and accommodated in the gas-outlet groove 3216, for detecting the polluted gas introduced into the gas-outlet groove 3216. In some embodiments, the particulate sensor 325 is a $PM_{2.5}$ sensor for detecting information of particulate matters. In some embodiments, the gas sensor 327 is a volatile-organic-compound sensor for detecting information of carbon dioxide or total volatile organic compounds. In some other embodiments, the gas sensor 327 is a formaldehyde sensor for detecting information of formaldehydes. In some other embodiments, the gas sensor 327 is a bacteria sensor for detecting information of bacteria or fungi. In some other embodiments, the gas sensor 327 is a virus senor for detecting information of viruses.

The piezoelectric actuator 322 mentioned above is accommodated in the square-shaped gas-guiding-component loading region 3215 of the base 321. In addition, the gas-guiding-component loading region 3215 is in communication with the gas-inlet groove 3214. When the piezoelectric actuator 322 is enabled, the gas in the gas-inlet groove 3214 is inhaled by the piezoelectric actuator 322, so that the gas flows into the piezoelectric actuator 322 and is transported into the gas-outlet groove 3216 through the ventilation hole 3215a of the gas-guiding-component loading region 3215. The driving circuit board 323 mentioned above covers and attaches to the second surface 3212 of the base 321, and the laser component 324 is positioned and disposed on the driving circuit board 323, and is electrically connected to the driving circuit board 323. The particulate sensor 325 also is positioned and disposed on the driving circuit board 323, and is electrically connected to the driving circuit board 323. When the outer cover 326 covers the base 321, the inlet opening 3261a is spatially corresponding to the gas-inlet 3214a of the base 321, and the outlet opening 3261b is spatially corresponding to the gas-outlet 3216a of the base 321.

The piezoelectric actuator 322 mentioned above includes a gas-injection plate 3221, a chamber frame 3222, an actuator element 3223, an insulation frame 3224 and a conductive frame 3225. In the embodiment, the gas-injection plate 3221 is made by a flexible material and includes a suspension plate 3221a and a hollow aperture 3221b. The suspension plate 3221a is a sheet structure and is permitted to undergo a bending deformation. Preferably but not exclusively, the shape and the size of the suspension plate 3221a are corresponding to the inner edge of the gas-guiding-component loading region 3215, but not limited thereto. The hollow aperture 3221b passes through a center of the suspension plate 3221a, so as to allow the gas to flow therethrough. Preferably but not exclusively, the shape of the suspension plate 3221a is selected from the group consisting of a square, a circle, an ellipse, a triangle and a polygon.

The chamber frame 3222 mentioned above is carried and stacked on the gas-injection plate 3221. In addition, the shape of the chamber frame 3222 is corresponding to the gas-injection plate 3221. The actuator element 3223 is carried and stacked on the chamber frame 3222 and collaboratively defines a resonance chamber 3226 with the gas-injection plate 3221 and the suspension plate 3221a. The insulation frame 3224 is carried and stacked on the actuator element 3223 and the appearance of the insulation frame 3224 is similar to that of the chamber frame 3222. The conductive frame 3225 is carried and stacked on the insulation frame 3224, and the appearance of the conductive frame 3225 is similar to that of the insulation frame 3224. In addition, the conductive frame 3225 includes a conducting pin 3225a extended outwardly from an outer edge of the conducting pin 3225a and a conducting electrode 3225b extended inwardly from an inner edge of the conductive frame 3225.

Moreover, the actuator element 3223 further includes a piezoelectric carrying plate 3223a, an adjusting resonance plate 3223b and a piezoelectric plate 3223c. The piezoelectric carrying plate 3223a is carried and stacked on the chamber frame 3222. The adjusting resonance plate 3223b is carried and stacked on the piezoelectric carrying plate 3223a. The piezoelectric plate 3223c is carried and stacked on the adjusting resonance plate 3223b. The adjusting resonance plate 3223b and the piezoelectric plate 3223c are accommodated in the insulation frame 3224. The conducting electrode 3225b of the conductive frame 3225 is electrically connected to the piezoelectric plate 3223c. In the embodiment, the piezoelectric carrying plate 3223a and the adjusting resonance plate 3223b are made by a conductive material. The piezoelectric carrying plate 3223a includes a piezoelectric pin 3223d. The piezoelectric pin 3223d and the conducting pin 3225a are electrically connected to a driving circuit (not shown) of the driving circuit board 323, so as to receive a driving signal (which can be a driving frequency and a driving voltage). Through this structure, a circuit is formed by the piezoelectric pin 3223d, the piezoelectric carrying plate 3223a, the adjusting resonance plate 3223b, the piezoelectric plate 3223c, the conducting electrode 3225b, the conductive frame 3225 and the conducting pin 3225a for transmitting the driving signal. Moreover, the insulation frame 3224 provides insulation between the conductive frame 3225 and the actuator element 3223, so as to avoid the occurrence of a short circuit. Thereby, the driving signal is transmitted to the piezoelectric plate 3223c. After receiving the driving signal, the piezoelectric plate 3223c deforms due to the piezoelectric effect, and the piezoelectric carrying plate 3223a and the adjusting resonance plate 3223b are further driven to bend and vibrate in the reciprocating manner.

The adjusting resonance plate 3223b is located between the piezoelectric plate 3223c and the piezoelectric carrying plate 3223a and served as a cushion between the piezoelectric plate 3223c and the piezoelectric carrying plate 3223a. Thereby, the vibration frequency of the piezoelectric carrying plate 3223a is adjustable. Basically, the thickness of the adjusting resonance plate 3223b is greater than the thickness of the piezoelectric carrying plate 3223a, and the thickness of the adjusting resonance plate 3223b is adjustable to adjust the vibration frequency of the actuator element 3223 accordingly. In the embodiment, the gas-injection plate 3221, the chamber frame 3222, the actuator element 3223, the insulation frame 3224 and the conductive frame 3225 are stacked and positioned in the gas-guiding-component loading region 3215 sequentially, so that the piezoelectric actuator 322 is supported and positioned in the gas-guiding-component loading region 3215. A clearance 3221c is defined by the piezoelectric actuator 322 between the suspension plate 3221a and an inner edge of the gas-guiding-component loading region 3215 for gas flowing therethrough.

A flowing chamber 3227 is formed between the gas-injection plate 3221 and the bottom surface of the gas-guiding-component loading region 3215. The flowing chamber 3227 is in communication with the resonance chamber 3226 located between the actuator element 3223, the gas-injection plate 3221 and the suspension plate 3221a through the hollow aperture 3221b of the gas-injection plate 3221. By controlling the vibration frequency of the gas in the resonance chamber 3226 to be close to the vibration frequency of the suspension plate 3221a, the Helmholtz resonance effect is generated between the resonance chamber 3226 and the suspension plate 3221a, so as to improve the efficiency of gas transportation. When the piezoelectric plate 3223c moves away from the bottom surface of the gas-guiding-component loading region 3215, the suspension plate 3221a of the gas-injection plate 3221 is driven to move away from the bottom surface of the gas-guiding-component loading region 3215 by the piezoelectric plate 3223c. In that, the volume of the flowing chamber 3227 is expanded rapidly, the internal pressure of the flowing chamber 3227 is decreased and generates a negative pressure, and the gas outside the piezoelectric actuator 322 is inhaled through the clearance 3221c and enters the resonance chamber 3226 through the hollow aperture 3221b. Consequently, the pressure in the resonance chamber 3226 is increased to generate a pressure gradient. When the suspension plate 3221a of the gas-injection plate 3221 is driven by the piezoelectric plate 3223c to move toward the bottom surface of the gas-guiding-component loading region 3215, the gas in the resonance chamber 3226 is discharged out rapidly through the hollow aperture 3221b, and the gas in the flowing chamber 3227 is compressed, thereby the converged gas is quickly and massively ejected out of the flowing chamber 3227 under the condition close to an ideal gas state of the Benulli's law, and transported to the ventilation hole 3215a of the gas-guiding-component loading region 3215.

Figure 9A:
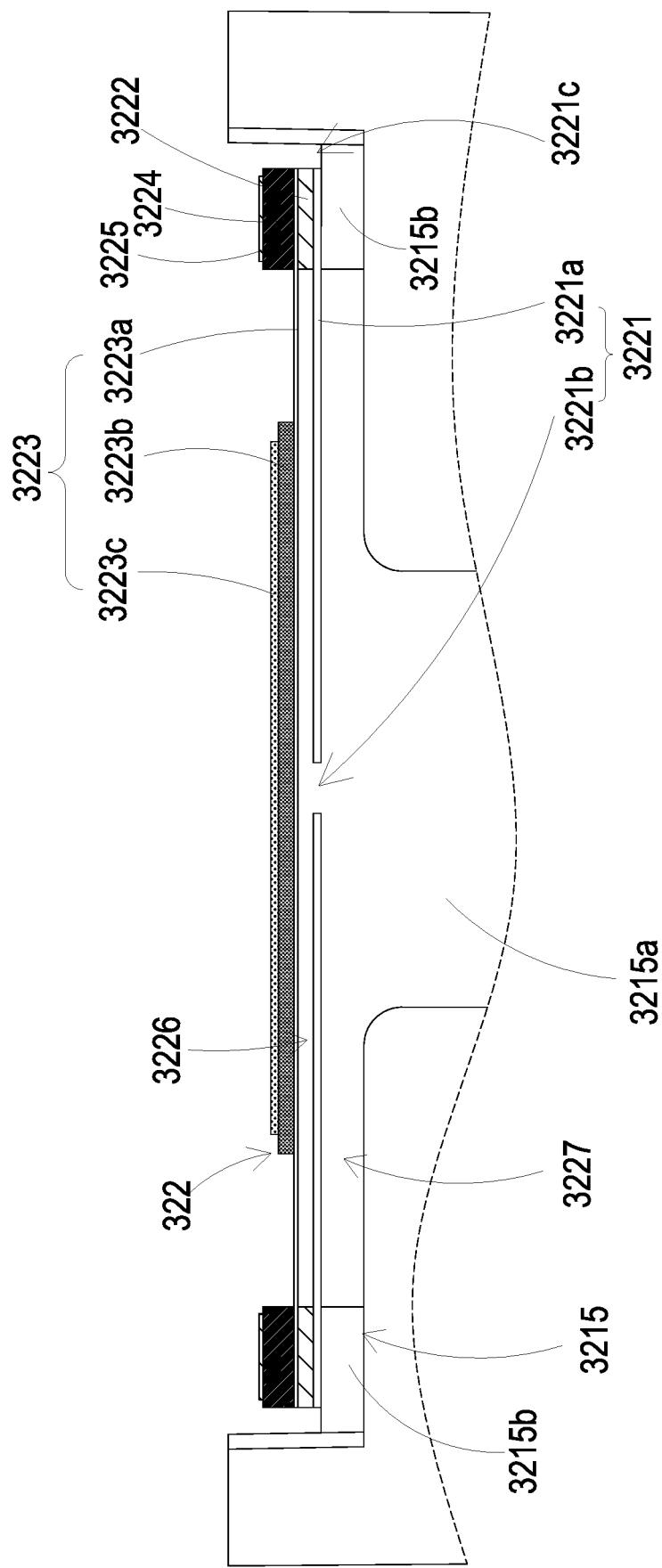
FIG. 9A is a first schematic cross-sectional view illustrating the operation step of the piezoelectric actuator according to an embodiment of the present disclosure.
Figure 9B:
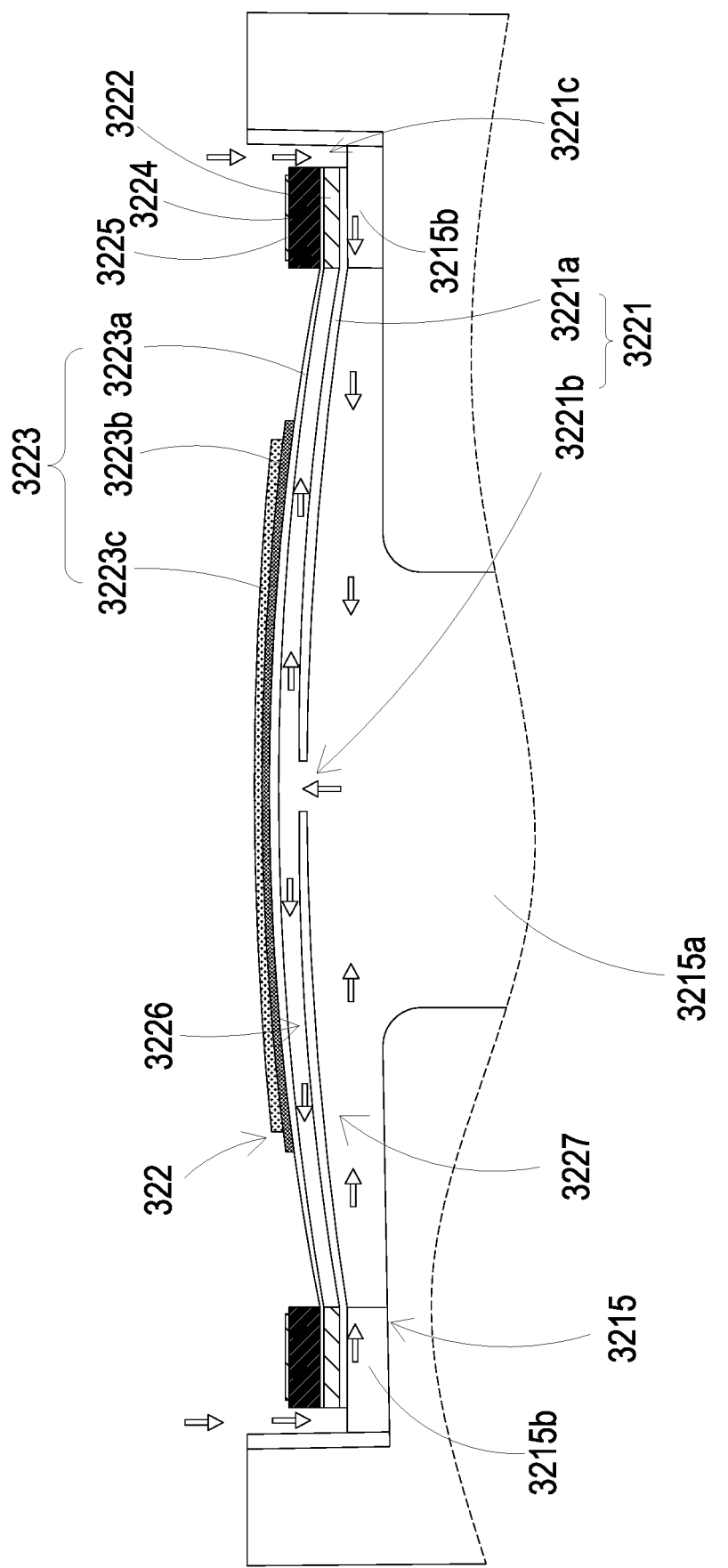
FIG. 9B is a second schematic cross-sectional view illustrating the operation step of the piezoelectric actuator according to the embodiment of the present disclosure.
Figure 9C:
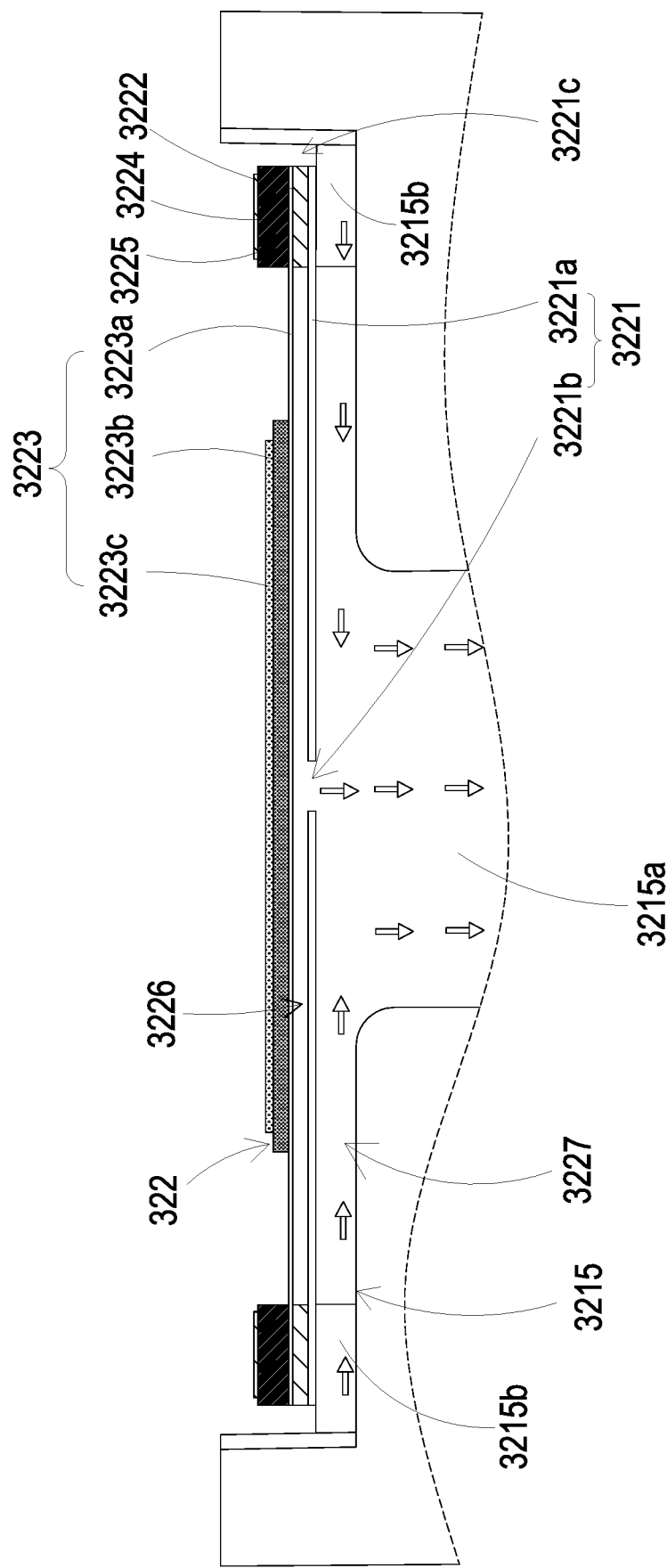
FIG. 9C is a third schematic cross-sectional view illustrating the operation step of the piezoelectric actuator according to the embodiment of the present disclosure.
Figure 10A:
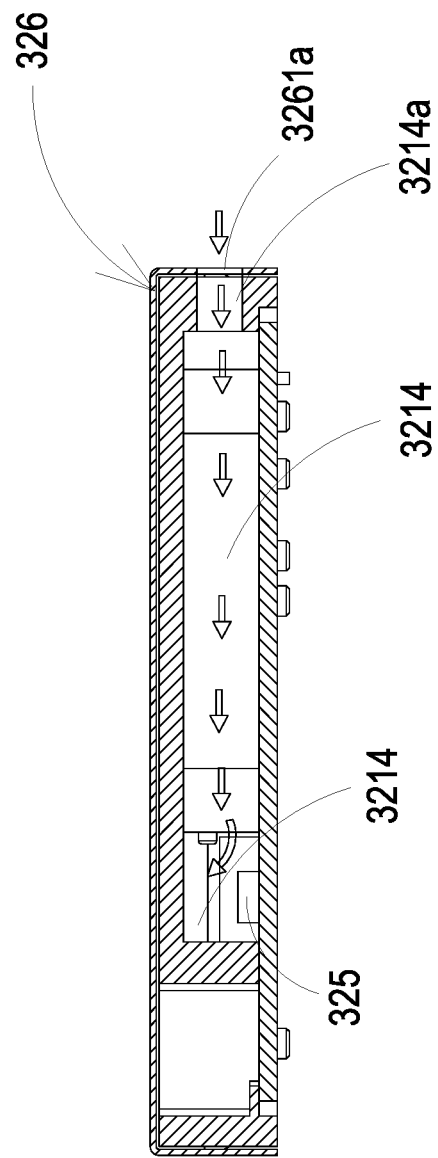
FIG. 10A is a first schematic cross-sectional view illustrating the assembled gas detection main body according to an embodiment of the present disclosure.
Figure 10B:
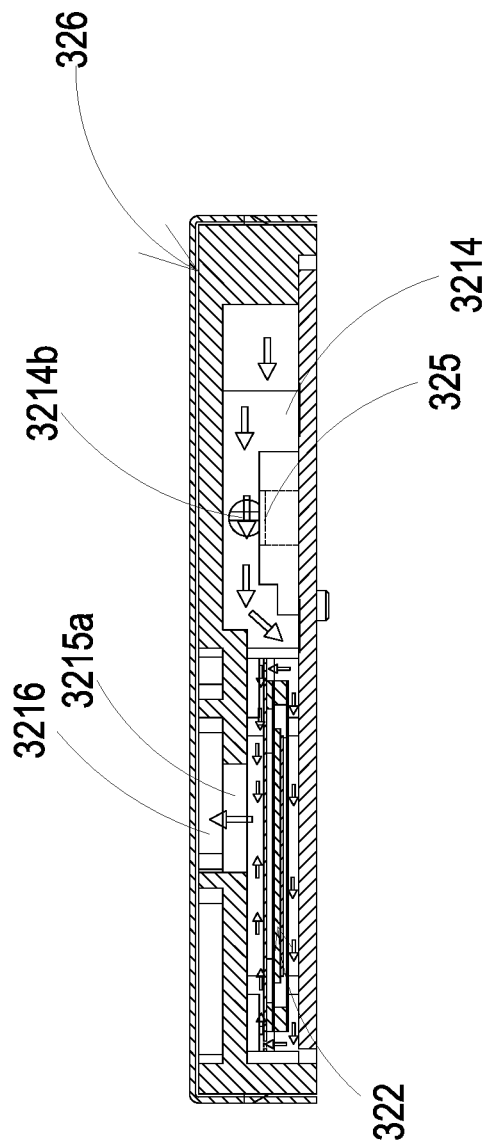
FIG. 10B is a second schematic cross-sectional view illustrating the assembled gas detection main body according to the embodiment of the present disclosure.
Figure 10C:
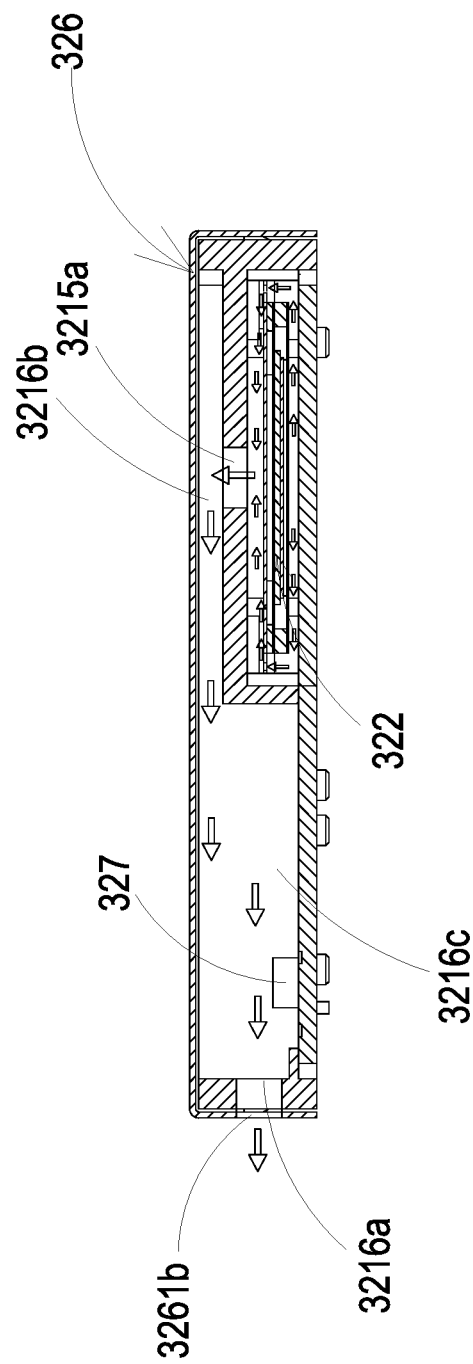
FIG. 10C is a third schematic cross-sectional view illustrating the assembled gas detection main body according to the embodiment of the present disclosure.
Figure 11:
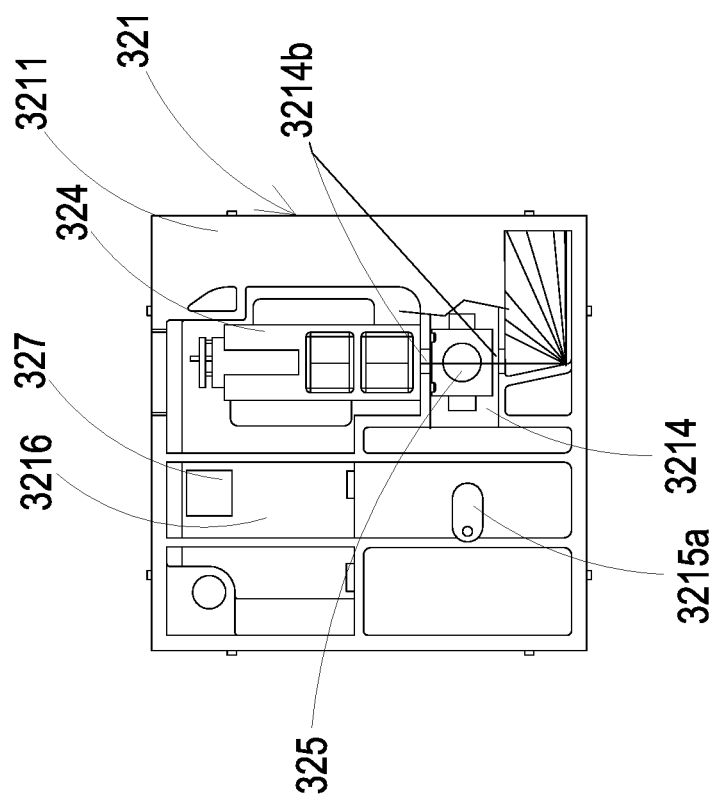
FIG. 11 is a schematic view illustrating a light beam path emitted by a laser component of the gas detection main body according to an embodiment of the present disclosure.

By repeating the operation steps shown in FIG. 9B and FIG. 9C, the piezoelectric plate 3223c is driven to vibrate in a reciprocating manner. According to the principle of inertia, since the gas pressure inside the resonance chamber 3226 is lower than the equilibrium gas pressure after the converged gas is ejected out, the gas is introduced into the resonance chamber 3226 again. Moreover, the vibration frequency of the gas in the resonance chamber 3226 is controlled to be close to the vibration frequency of the piezoelectric plate 3223c, so as to generate the Helmholtz resonance effect to achieve the gas transportation at high speed and in large quantities.

Furthermore, as shown in FIG. 10A to FIG. 10C and FIG. 11, the gas is inhaled through the inlet opening 3261a of the outer cover 326, flows into the gas-inlet groove 3214 of the base 321 through the gas-inlet 3214a, and is transported to the position of the particulate sensor 325. Furthermore, the piezoelectric actuator 322 is enabled continuously to inhale the gas into the inlet path, and facilitate the external gas to be introduced rapidly, flowed stably, and be transported above the particulate sensor 325. At this time, a projecting light beam emitted from the laser component 324 passes through the transparent window 3214b and enters into the gas-inlet groove 3214 to irritate the suspended particles contained in the gas flowing above the particulate sensor 325 in the gas-inlet groove 3214. When the suspended particles contained in the gas are irradiated and generate scattered light spots, the scattered light spots are received and calculated by the particulate sensor 325 for obtaining related information about the sizes and the concentrations of the suspended particles contained in the gas. Moreover, the gas above the particulate sensor 325 is continuously driven and transported by the piezoelectric actuator 322, flows into the ventilation hole 3215a of the gas-guiding-component loading region 3215, and is transported to the gas-outlet groove 3216. Finally, after the gas flows into the gas-outlet groove 3216, the gas is continuously transported into the gas-outlet groove 3216 by the piezoelectric actuator 322, and the gas in the gas-outlet groove 3216 is pushed and discharged out through the gas-outlet 3216a and the outlet opening 3261b.

In summary, the air purification device according to the present disclosure includes the device main body 1 and the gas detection module 3 is disposed in the device main body 1. When the particulate sensor 325 of the gas detection module 3 detects the harmful gases contained in the air, the gas guider 4 is intelligently enabled to guide the air to enter the device main body 1. The activated carbon layer 21a and the zeolite layer 21b included in the purification filter 2 disposed in the device main body 1 filter and purify the suspended particles (particulate matter, $PM_{2.5}$) and the volatile organic compounds (VOCs) contained in the harmful gases and generate the purified gas, so as to reduce the opportunity of breathing the harmful gases in the activity space. Therefore, the air purification device of the present invention takes advantage of the combination of the activated carbon layer 21a and the zeolite layer 21b included in the purification filter 2 cooperated with the gas guider 4 in the device main body 1 to improve the efficiency of providing a purified and clean gas in the activity space.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An air purification device, comprising:
 a device main body comprising at least one gas-inlet opening and at least one gas-outlet opening, wherein the at least one gas-outlet opening is a non-closed opening and in fluid communication to an outside;
 a purification filter disposed in the device main body and comprising at least one activated carbon layer and at least one zeolite layer stacked on each other, wherein the activated carbon layer filters and absorbs suspended particles contained in an air introduced into the device main body through the gas-inlet opening, and the zeolite layer includes porous structures with hydrophobic property for controlling and absorbing volatile organic compounds contained in the air introduced into the device main body through the gas-inlet opening, thereby a purified gas is generated from the air and is discharged through the gas-outlet opening;

a gas detection module disposed in the device main body for detecting and obtaining a gas quality data of the air passing through the gas-inlet opening and outputting the gas quality data, wherein the gas detection module comprises a control circuit board, a gas detection main body, a microprocessor and a communicator, and the gas detection main body, the microprocessor and the communicator are integrally packaged on the control circuit board and electrically connected with each other; and a gas guider disposed in the device main body adjacent to the gas-outlet opening for guiding the air to enter the device main body and pass through the purification filter, so as to filter and purify the air, generate the purified gas and discharge the purified gas through the gas-outlet opening, wherein the gas detection module is configured to provide the gas quality data to the gas guider, so as to allow the gas guider to intelligently determine whether it is to be enabled or disabled to guide the air for filtration and purification, wherein the gas detection module is configured to transmit the gas quality data of the air to an external connection device for displaying the gas quality data of the air and providing an alert notification, wherein the microprocessor receives, computes and processes the gas quality data detected by the gas detection module for controlling the gas guider to be enabled or disabled, the gas quality data received by the microprocessor is transmitted to the external connection device by the communicator, and the external connection device receives and records the gas quality data for providing the alert notification.

2. The air purification device as claimed in claim 1, wherein the purification filter comprises a single activated carbon layer and a plurality of the zeolite layers stacked on each other for improving the efficiency of absorption and purification of the suspended particles and the volatile organic compounds contained in the air introduced into the device main body.

3. The air purification device as claimed in claim 1, wherein the purification filter comprises a plurality of the activated carbon layers and a single zeolite layer stacked on each other for improving the efficiency of absorption and purification of the suspended particles and the volatile organic compounds contained in the air introduced into the device main body.

4. The air purification device as claimed in claim 1, wherein the purification filter comprises a plurality of the activated carbon layers and a plurality of the zeolite layers stacked on each other for improving the efficiency of absorption and purification of the suspended particles and the volatile organic compounds contained in the air introduced into the device main body.

5. The air purification device as claimed in claim 1, wherein the gas detection main body comprises:
   a base comprising:
   a first surface;
   a second surface opposite to the first surface;
   a laser loading region hollowed out from the first surface to the second surface;
   a gas-inlet groove concavely formed from the second surface and disposed adjacent to the laser loading region, wherein the gas-inlet groove comprises a gas-inlet and a transparent window opened on two lateral walls thereof and in communication with the laser loading region;
   a gas-guiding-component loading region concavely formed from the second surface and in communication with the gas-inlet groove, and having a ventilation hole penetrated a bottom surface thereof, wherein each of four corners of the gas-guiding-component loading region respectively comprises a positioning protrusion; and
   a gas-outlet groove concavely formed from a region of the first surface spatially corresponding to the bottom surface of the gas-guiding-component loading region and hollowed out from the first surface to the second surface in a region where the first surface is misaligned with the gas-guiding-component loading region, wherein the gas-outlet groove is in communication with the ventilation hole and comprises a gas-outlet mounted thereon;
   a piezoelectric actuator accommodated in the gas-guiding-component loading region;
   a driving circuit board covering and attaching to the second surface of the base;
   a laser component positioned and disposed on the driving circuit board and electrically connected to the driving circuit board, and accommodated in the laser loading region, wherein a light beam path emitted by the laser component passes through the transparent window and extends in an orthogonal direction perpendicular to the gas-inlet groove;
   a particulate sensor positioned and disposed on the driving circuit board and electrically connected to the driving circuit board, and accommodated in the gas-inlet groove at a region in an orthogonal direction perpendicular to the light beam path emitted by the laser component for detecting suspended particles in the air passing through the gas-inlet groove and irradiated by a light beam emitted from the laser component; and
   an outer cover covering the first surface of the base and comprising a lateral plate, wherein the lateral plate comprises an inlet opening and an outlet opening at positions spatially corresponding to respectively the gas-inlet and the gas-outlet of the base, wherein the inlet opening is spatially corresponding to the gas-inlet of the base and the outlet opening is spatially corresponding to the gas-outlet of the base,
   wherein the first surface of the base is covered by the outer cover, and the second surface of the base is covered by the driving circuit board, so that an inlet path is defined by the gas-inlet groove and an outlet path is defined by the gas-outlet groove, thereby the piezoelectric actuator introduces the air outside the gas-inlet of the base into the inlet path defined by the gas-inlet groove through the inlet opening, the particulate sensor detects a concentration of the suspended particles contained in the air, and the air is guided by the piezoelectric actuator to enter the outlet path defined by the gas-outlet groove through the ventilation hole and discharged through the gas-outlet of the base and the outlet opening.

6. The air purification device as claimed in claim 5, wherein the particulate sensor is a PM2.5 sensor.

7. The air purification device as claimed in claim 5, wherein the piezoelectric actuator comprises:
   a gas-injection plate comprising a suspension plate capable of bending and vibrating and a hollow aperture formed at a center of the suspension plate;
   a chamber frame carried and stacked on the suspension plate;

an actuator element carried and stacked on the chamber frame and comprising a piezoelectric carrying plate, an adjusting resonance plate and a piezoelectric plate, wherein the piezoelectric carrying plate is carried and stacked on the chamber frame, the adjusting resonance plate is carried and stacked on the piezoelectric carrying plate, and the piezoelectric plate is carried and stacked on the adjusting resonance plate, and after receiving a voltage, the piezoelectric carrying plate and the adjusting resonance plate are driven to bend and vibrate in a reciprocating manner;

an insulation frame carried and stacked on the actuator element; and a conductive frame carried and stacked on the insulation frame;

wherein the gas-injection plate is supported and positioned on the positioning protrusions of the gas-guiding-component loading region, so that a clearance surrounding the gas-injection plate is defined for flowing the gas therethrough, a flowing chamber is formed between the gas-injection plate and the bottom surface of the gas-guiding-component loading region, and a resonance chamber is collaboratively defined by the actuator element, the chamber frame and the suspension plate, thereby through driving the actuator element to drive the gas-injection plate to resonate, the suspension plate of the gas-injection plate generates vibration and displacement in a reciprocating manner, so as to inhale the gas into the flowing chamber through the clearance and then eject out for completing a gas flow transmission.

8. The air purification device as claimed in claim 5, further comprising a volatile-organic-compound sensor positioned and disposed on the driving circuit board and electrically connected to the driving circuit board, and accommodated in the gas-outlet groove, so as to detect the volatile organic compounds contained in the air guided through the outlet path.

\* \* \* \* \*